(12) United States Patent
Muller et al.

(10) Patent No.: US 10,227,294 B2
(45) Date of Patent: Mar. 12, 2019

(54) METHOD FOR CONTROLLING THE PROCESS FOR MAKING ISOCYANATES

(71) Applicant: HUNTSMAN INTERNATIONAL LLC, The Woodlands, TX (US)

(72) Inventors: Peter Muller, Hellevoetsluis (NL); Robert Henry Carr, Bertem (BE)

(73) Assignee: HUNTSMAN INTERNATIONAL LLC, The Woodlands, TX (US)

( * ) Notice: Subject to any disclaimer, the term of this patent is extended or adjusted under 35 U.S.C. 154(b) by 0 days.

(21) Appl. No.: 15/767,870

(22) PCT Filed: Sep. 28, 2016

(86) PCT No.: PCT/EP2016/073103
§ 371 (c)(1),
(2) Date: Apr. 12, 2018

(87) PCT Pub. No.: WO2017/063883
PCT Pub. Date: Apr. 20, 2017

(65) Prior Publication Data
US 2018/0297940 A1    Oct. 18, 2018

(30) Foreign Application Priority Data

Oct. 16, 2015  (EP) .................................... 15190116

(51) Int. Cl.
| | |
|---|---|
| *C07C 263/10* | (2006.01) |
| *C08G 18/76* | (2006.01) |
| *B01J 19/00* | (2006.01) |
| *C07C 265/14* | (2006.01) |

(52) U.S. Cl.
CPC ........... *C07C 263/10* (2013.01); *B01J 19/002* (2013.01); *C08G 18/7664* (2013.01); *B01J 2219/00006* (2013.01); *B01J 2219/00186* (2013.01); *B01J 2219/00202* (2013.01); *B01J 2219/00231* (2013.01); *C07C 265/14* (2013.01)

(58) Field of Classification Search
CPC .... C07C 263/10; C07C 265/14; B01J 19/002; B01J 2219/00202; B01J 2219/00186; B01J 2219/00231; B01J 2219/00006; C08G 18/7664
See application file for complete search history.

(56) References Cited

U.S. PATENT DOCUMENTS

| 8,519,179 B2 | 8/2013 | Shelling et al. |
| 2009/0175121 A1 | 7/2009 | Rausch et al. |
| 2013/0144081 A1* | 6/2013 | Kintrup ................. C07C 263/10 558/302 |

FOREIGN PATENT DOCUMENTS

| EP | 1758673 A1 | 3/2007 |
| EP | 1868712 B1 | 10/2008 |
| WO | 2012050858 A1 | 4/2012 |

* cited by examiner

*Primary Examiner* — Yevgeny Valenrod
*Assistant Examiner* — Blaine G Doletski
(74) *Attorney, Agent, or Firm* — Huntsman International LLC; Robert Diaz

(57) ABSTRACT

The invention relates to a method for preparing an aromatic polyisocyanate in an isocyanate plant comprising a reaction section for a phosgenation reaction, wherein a primary aromatic amine is reacted with phosgene compounds in a reaction section to obtain an isocyanate comprising reaction product and wherein $CO_2$ concentration in the gases coming from the reaction section is measured and analyzed, and wherein the conditions in the phosgenation reaction are adjusted in case the $CO_2$ concentration in the gases coming from the reaction section is higher than a background $CO_2$ concentration.

15 Claims, 4 Drawing Sheets

METHOD FOR CONTROLLING THE PROCESS FOR MAKING ISOCYANATES

CROSS-REFERENCE TO RELATED APPLICATIONS

This application is the National Phase of International Application PCT/EP2016/073103 filed Sep. 28, 2016 which designated the U.S. and which claims priority to European App. Serial No. 15190116.2 filed Oct. 16, 2015. The noted applications are incorporated herein by reference.

The present invention relates to a method for preparing aromatic polyisocyanates in an isocyanate plant by reacting a phosgene stream with one or more of the corresponding primary aromatic amine stream. In particular, the invention is related to the controlling of the reaction and adjusting the reaction conditions.

Isocyanates and isocyanate mixtures can be prepared by known processes by reacting primary amines with an excess of phosgene.

The starting materials are usually fed together with a solvent by means of an inlet into a reaction section, where the compounds are mixed and reacted in a reactor to form the corresponding isocyanate. After this reaction, the reaction mixture is passed to a work-up section of the plant which is located downstream of the reaction section and in which a work-up to give product streams comprising isocyanate, solvent and off gases is carried out. The worked-up purified solvent is usually fed back into the process.

There are by-products formed during the reaction of primary aromatic amines and phosgene compounds. These by-products provide an increased viscosity and are considered as "lost isocyanate groups" or "lost NCO" since these cannot contribute totally or only contribute partly to the formation of polyurethanes and other products derived from use of polyisocyanates.

The initial reaction of the primary aromatic amine with phosgene compounds is very fast. From the moment these compounds come in contact, the reaction starts. Very special mixing devices and special combinations of mixing devices and reactors have been developed in order to make the reaction efficient so that a minimum of by-products is formed. Such type of mixing devices are e.g. described in EP 1 868 712 B1 or in EP 1 758 673 A1.

To find out the efficiency of the formation of the aromatic polyisocyanates, the product entering the work up section and the (partially) worked up product is analyzed, by e.g. determining the NCO value, the hydrolysable chlorine value, the viscosity, acidity value etc. These are done by means of taking samples which are then brought to on-site laboratories, or via techniques that analyze the samples "on line". All these techniques are conventionally used and described.

There is still a need for further improvements and finding other ways to determine whether by-products are formed when aromatic polyisocyanates are prepared.

Furthermore, there is a need to analyse sooner whether by-products are formed in the production process of isocyanates so that the reaction conditions can be changed sooner to minimize further formation of by-products.

The above objects, amongst others, can be solved, at least partially, by a method according to claim 1.

In particular, the objectives amongst other objects can be solved by a first aspect of the invention which is a method for preparing an aromatic polyisocyanate in an isocyanate plant comprising a reaction section for a phosgenation reaction, the method comprising the steps of:

a) providing a primary aromatic amine stream and a phosgene stream via an inlet in the reaction section;
b) reacting the primary aromatic amine with the phosgene compounds in the reaction section to obtain an isocyanate comprising reaction product;
c1) measuring $CO_2$ concentration in the gases coming from the reaction section;
d1) analyzing the $CO_2$ concentration in the gases coming from the reaction section by comparing with a background $CO_2$ concentration;
e) adjusting conditions in the phosgenation reaction in case the $CO_2$ concentration in the gases coming from the reaction section is higher than the background $CO_2$ concentration and/or deviates with more than 2 vol %, preferably more than 1 vol %, more preferably more than 0.6 vol % in view of the total volume of the gases coming from the reaction section.

The inventors surprisingly found that already in the reaction section, it can be determined whether by-products are formed. This is done by measuring the $CO_2$ concentration of the gas phase in the reaction section and by adjusting the reaction conditions as a response to the results of the analysis. By-products that are formed during reaction of primary aromatic amines with phosgene compounds and/or subsequent reactions with phosgene compounds, are chloroformamidine compounds and chloroformamidine N-carbonyl chloride (CCC) compounds. These by-products are formed through reaction of an amine group of the primary aromatic amine with an isocyanate group of the formed aromatic isocyanate, which forms a urea compound. The urea compound reacts further with phosgene compounds and forms chloroformamidine and chloroformamidine N-carbonyl chloride. When these by-products are formed, also $CO_2$ is formed.

In the reaction section a gas phase is present and can be removed. The gases comprise mainly phosgene compounds, hydrogen chloride, carbon monoxide and carbon dioxide. Some of the $CO_2$ in the reaction section is present due to the formation of by-products. The phosgene stream provided for reaction with the primary aromatic amine often also comprises $CO_2$ and some of the $CO_2$ in the gases of the reaction section derives from the phosgene stream. An increased $CO_2$ level found in the gases of the reaction section compared to the level of $CO_2$ derived from the initially provided phosgene stream means that the reaction conditions are no longer optimal and (more) by-products are being formed. Further formation of the by-products can be prevented by changing the conditions of the phosgenation reaction.

In a second aspect the invention is also related to a method for preparing an aromatic polyisocyanate in an isocyanate plant comprising a reaction section for a phosgenation reaction and a work-up section which is downstream of the reaction section and treats the isocyanate comprising stream, the method comprising the steps of:

a) providing a primary aromatic amine stream and a phosgene stream via an inlet in the reaction section;
b) reacting the primary aromatic amines with the phosgene compounds in the reaction section to obtain an isocyanate comprising reaction product;
c2) measuring $CO_2$ concentration in the gases coming from the reaction section and the work-up section;
d2) analyzing the $CO_2$ concentration in the gases coming from the reaction section and the work-up section by comparing with a background $CO_2$ concentration;
e) adjusting conditions in the phosgenation reaction in case the $CO_2$ concentration in the gases coming from the reaction section and the work up section is higher than the background $CO_2$ concentration and/or deviates with more than 2 vol %, preferably more than 1 vol %, more preferably more than 0.6 vol % in view of the total volume of the gases coming from the reaction section.

According to this invention the background $CO_2$ concentration is the $CO_2$ that derives from the phosgene stream. The background $CO_2$ may further comprise $CO_2$ that derives from $H_2O$ that enters via the primary aromatic amine stream which $H_2O$ can react further in the reaction section so that also $CO_2$ is formed. Not all the $H_2O$ reacts further in the reaction section, and only a small amount of $CO_2$ is formed. The background $CO_2$ mainly derives from the phosgene stream. Therefore to measure the background $CO_2$ concentration, it is often sufficient only to measure the $CO_2$ in the phosgene stream. Note that when a very high amount of $CO_2$ is measured in the gases coming from the reaction section and/or work up section, this is often a sign that there is a water ingress or a too high amount of water is entering via the primary aromatic amine stream. This needs other adjustments of the reaction conditions than those described in this invention. The $CO_2$ concentration coming from the reaction section or the reaction section and the work-up section that is being measured is the sum of the background $CO_2$ concentration and the $CO_2$ that comes off when by-products are formed. Without being bound to a theory and by way of example the by-products can be formed in a way as is shown in reaction scheme (I) wherein only the reacting functional groups are shown and R represents the rest of the amine or isocyanate molecule.

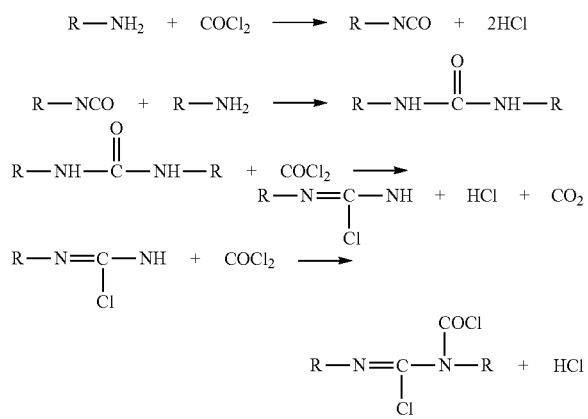

The $CO_2$ concentration is then analysed by comparing with the background $CO_2$ concentration. When the $CO_2$ concentration is higher than the background $CO_2$ concentration, then the process conditions can be adjusted. The adjustment can be done in case the $CO_2$ concentration in the gases coming from the reaction section (off-gases) is higher than the background $CO_2$ concentration and/or deviates with more than 2 vol %, preferably more than 1 vol %, more preferably more than 0.6 vol % or deviates with more than 0.1 vol %; 0.2 vol %; 0.3 vol %; 0.4 vol %; 0.5 vol %, in view of the total volume of the gases coming from the reaction section. When the adjustment is only done e.g. when the deviation between background and off-gases is more than e.g. 0.6 vol %, this means that a small amount of by-products will be present in the formed isocyanates. The reason why one can decide not to reduce the amount of by-products even more depends on several factors such as equipment of the plant, efficiency requirement of the production, and because the product quality may be acceptable for a given use.

As described above, the $CO_2$ background concentration is mainly the $CO_2$ that enters the reaction section via the phosgene stream. A typical background $CO_2$ concentration is between 0 and 1 vol %, such as between 0 and 0.5 vol %; between 0 and 0.1 vol %, or between 0 and 0.005 vol %, based on the total volume of the gases coming from the reaction section. This background concentration depends on the reaction conditions that are used to make the phosgene compounds and can be different in other phosgene plants.

According to this invention, the reaction section is the section in an isocyanate plant where the phosgene stream and a stream comprising primary aromatic amine come together and react to form an isocyanate comprising stream. The reaction section comprises a reactor. All customary reactors known from the prior art which are suitable for preparing isocyanates are possible here.

For the purposes of the present invention, the term "work-up section" refers to the section in an isocyanate plant which is downstream of the reaction section and treats the isocyanate comprising stream that is conveyed from the reaction section further to obtain at least three streams comprising respectively predominantly isocyanate, predominantly solvent and predominantly off-gases including hydrogen chloride. In the work-up section one or more column-like systems are arranged for separation of isocyanate, solvent and, if appropriate, by-product. Other devices may optionally be used, for example, membrane-based units. The reaction mixture, which consists essentially of the isocyanates, the solvent, hydrogen chloride and phosgene compounds, is separated into its constituents in this section of the respective plant by means of distillation, rectification, absorption, use of semipermeable membrane techniques, and/or if appropriate, thermal residue treatment in kneaders or paddle dryers, and other techniques described and known by the person skilled in the art, with the solvent being able to be returned to the reaction section of the plant.

In the second aspect of the invention, the gas streams that appear during the work-up are analysed to measure the $CO_2$ concentration. The sum of the $CO_2$ concentration measured in the gases coming from the reaction section and the work-up section is then compared with the background $CO_2$ concentration. It is possible to measure the $CO_2$ concentration in the gases coming from the reaction section and the work-up section separately and then make the sum. It is also possible that the gases coming from the work-up section are combined with the gases coming from the reaction section and that the $CO_2$ concentration of the combined gas stream is measured. The $CO_2$ that is found in the gases coming from the work-up section mainly derives from $CO_2$ that was present in the liquid stream that comes from the reaction section.

Suitable amines are in principle all primary amines which can react in a suitable way with phosgene compounds to form polyisocyanates. All linear or branched, saturated or unsaturated aromatic primary monoamines or polyamines which can be reacted with phosgene compounds to form isocyanates are suitable. Examples of suitable amines are aniline, phenylenediamine, p-toluidine, 1,5-naphthylenediamine, 2,4- or 2,6-tolylenediamine or mixtures thereof, 4,4'-, 2,4'- or 2,2'-diphenylmethanediamine or mixtures thereof and also higher molecular weight isomeric, oligomeric or polymeric derivatives of the abovementioned amines and polyamines.

According to this invention aromatic polyisocyanates comprise also diisocyanates such as 4,4', 2,4' and 2,2'MDI isomers; 2,4 and 2,6 TDI isomers. The polyisocyanates according to this invention are those that can be formed by phosgenation of the above described aromatic primary amines. Examples of aromatic primary isocyanates are phenylenediisocyanate, methylphenyldiisocyanate, 1,5-naphthylenediisocyanate, 2,4- or 2,6-TDI or mixtures thereof, 4,4'-, 2,4'- or 2,2'-MDI or mixtures thereof and also higher molecular weight isomeric, oligomeric or polymeric derivatives of the abovementioned isocyanates.

The phosgene stream comprises phosgene compounds (i.e. $COCl_2$, $COClBr$ or $COBr_2$) which is optionally mixed with a solvent. A typical solvent that is used in an isocyanate plant is monochlorobenzene (MCB). Also other solvents are suitable like dichlorobenzenes, e.g. o-dichlorobenzene and p-dichlorobenzene, trichlorobenzene, the corresponding toluenes and xylenes, chloroethylbenzene, monochlorobiphenyl, $\alpha$- and $\beta$-naphthyl chloride and dialkyl phthalates such as diethyl isophthalate. The solvents may be used individually or as mixtures.

The embodiments described below are embodiments of both the first and second aspects. A skilled person will realize that some of the embodiments can be combined to obtain adjustment of the reaction conditions so that the $CO_2$ concentration is decreased.

In one embodiment the adjustment of the conditions of the phosgenation reaction is via adjusting a mixing nozzle. In this embodiment the inlet comprises a mixing nozzle. The nozzle has at least two conduits, having a conduit end and an end opening at the conduit end, wherein at least one conduit provides the phosgene stream and at least one other conduit provides the primary aromatic amine stream, each stream forming a jet when released from the conduit opening and the phosgene stream jet and the aromatic amine stream jet come in contact with each other and are able to mix. This way a new mixing jet stream is formed wherein the primary aromatic amines and phosgene compound start to react. This new reacting jet stream forms part of the reaction section. The conduits of the mixing nozzle can comprise any of those described in the prior art such as circular or rectangular cross sectional conduits arranged concentrically, conduits that are directly opposed to each other, in a straight line or at some other angle so that the at least two jet streams impinge.

In case the $CO_2$ concentration in the gases coming from the reaction section is higher than the background $CO_2$ concentration in view of the total volume of the gases coming from the reaction section, then parts of the nozzle can be adjusted.

In one embodiment the adjustment of the mixing nozzle is adjusting at least one conduit end opening in the nozzle. With adjusting the conduit end opening of the nozzle it is meant that the conduit end opening is increased or decreased. It is possible that the conduit end opening of the conduit providing the phosgene stream is increased or decreased, the conduit end opening of the conduit providing the aromatic amine stream is increased or decreased, or both conduit end openings of the aromatic amine stream and phosgene stream are increased or decreased. In most of the cases, decreasing at least one of the conduit end openings will lead to a decrease of by-products and a decrease in $CO_2$ concentration. Adjusting the opening of the conduit ends of the nozzle will influence the initial mixing of the phosgene compound and the primary amine. When the mixing is insufficient, more by-products can be formed. This will be reflected in an increase of $CO_2$ concentration compared to the background $CO_2$ concentration. Decreasing the opening of the conduit ends of the nozzle will increase the power of the stream jet which may help improving the initial mixing of the reactants so that less by-products are formed. When the conduit end opening is decreased, more pressure is set on the streams, which causes a better mixing of the streams.

In another embodiment the adjustment of the mixing nozzle is adjusting the angle of at least two of the conduits, or the distance between at least two of the conduits. This embodiment may especially work for mixing nozzles wherein the conduits are directly opposed to each other, also known as impinging nozzles.

In yet another embodiment, the inlet comprises a mixing device which is a rotor-stator mixer. Such rotor-stator mixers are generally known. In this embodiment, adjusting conditions in the phosgenation reaction in case the $CO_2$ concentration in the gases coming from the reaction section and the work up section is higher than the background $CO_2$ concentration can be done by increasing or decreasing the speed of the rotor in the rotor-stator mixer.

In case other known inlets that comprises a mixing device are used, a skilled person will know other alternative adjustments of the mixing device that can be done in case the $CO_2$ concentration in the gases coming from the reaction section and the work up section is higher than the background $CO_2$ concentration.

In another embodiment, the adjustment of the conditions of the phosgenation reaction is adjusting the flow ratio of the primary aromatic amine stream and the phosgene stream at the inlet of the reaction section.

In yet another embodiment the adjustment of the conditions of the phosgenation reaction is adjusting the pressure in the reaction section. When the pressure is increased this may lead in most of the cases to a decrease of by-products. An increased pressure in the reactor causes more phosgene compound to be in the reaction solution. Usually the pressure in a phosgenation reaction is set around 1-11 bar, preferably 1-7 bar, and even more preferably 1-3.5 bar.

In yet another embodiment, the adjustment of the conditions of the phosgenation reaction is adjusting the temperature in the reaction section or in the phosgene stream and/or the primary amine stream. Also the temperature has an influence on the formation of the by-products and thus an increase of the $CO_2$ concentration. Changing the reaction conditions by changing the temperature in the reaction section or of the phosgene stream or primary amine stream may help to decrease the formation of by-products.

In yet another embodiment the adjustment of the conditions of the phosgenation reaction is adjusting the residence time of the reaction mixture of the primary aromatic amine compounds with the phosgene compounds in the reaction section. Most of the isocyanates plants have continuous process systems wherein the reactants enter the reaction section where they react to form an isocyanate comprising stream, which then continues as a stream to a work up section. By changing the reaction conditions so that the reactants remain longer in the reactor, it is possible that some of the deleterious by-products do not form.

In yet another embodiment, the adjustment of the conditions of the phosgenation reaction is adjusting the concentration of the primary aromatic amine in the primary aromatic amine stream and/or the phosgene compounds in the phosgene stream. When the primary aromatic amine stream is more diluted and/or the phosgene compounds in the phosgene stream are more diluted, the phosgenation reaction is more diluted, which may lead to less by-products.

In another embodiment the $CO_2$ concentration in the gases from the reaction section and/or the work-up section can be measured via infrared, gas chromatography, titration, near infrared, UV or other methods that are well known by a skilled person. Also the background $CO_2$ concentration in the phosgene stream can be measured via these techniques. As preferred example, infrared can be used by means of an infrared instrument having a sapphire window. Unreacted carbon monoxide and dichlorine may also be measured exiting the phosgene reactor at a suitable place.

The invention is further explained by the following figures and example that are non-limiting for the purpose of the invention.

Figure 1:
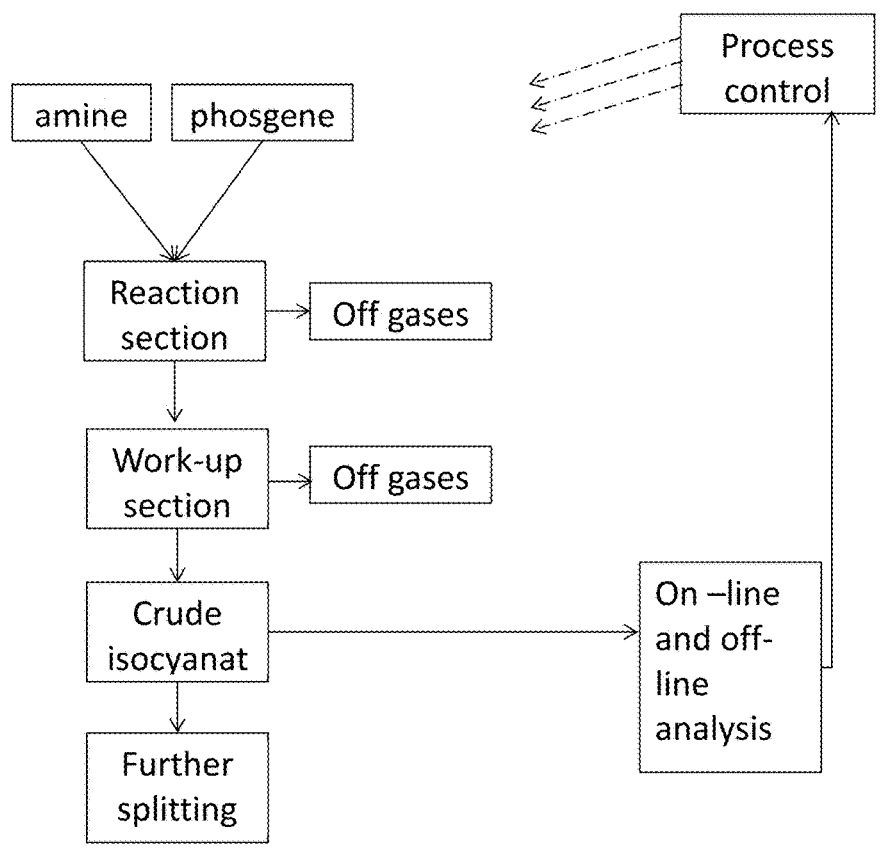
FIG. 1 is a flow diagram of a process of making isocyanates.

FIG. 1 shows a diagram where it is represented that the primary aromatic amine stream and the phosgene stream enter via an inlet into the reaction section. Gases formed in the reaction are taken off the reaction section (represented as "off gases"). The reactants enter the work-up section, also here gases that are formed are taken off. During work-up, the stream of crude isocyanates is formed. The crude isocyanates can be split further. All these steps are conventionally used and known by the skilled person. The crude isocyanates can be analysed via on-line or off-line analysis methods, to find out whether and how much by-products have been formed in the reaction section. When by-products are formed, the process controller can adjust the process conditions so that less by-products are formed.

Figure 2:
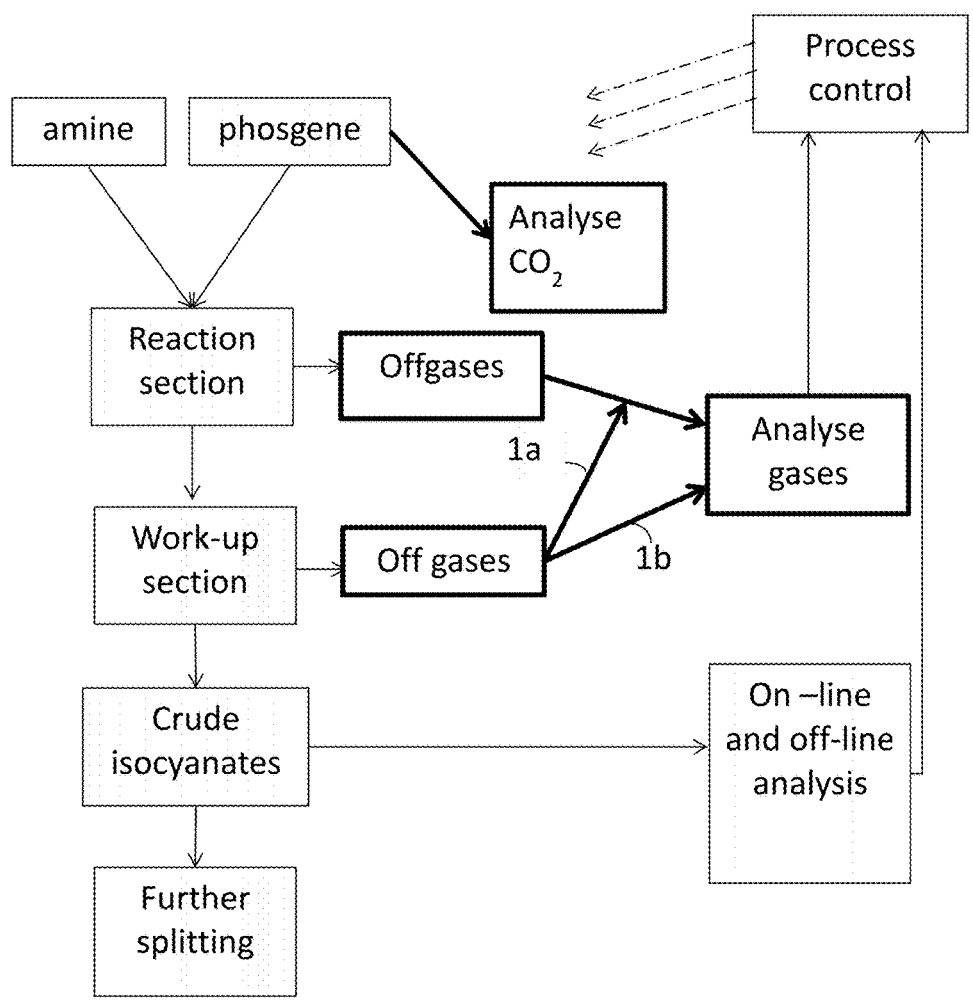
FIG. 2 is a flow diagram representing an embodiment of the invention.

FIG. 2 represents an embodiment of the invention. Here the same steps occur as in FIG. 1, but besides that the off gases coming from the reaction section can also be analysed to see whether $CO_2$ is formed in the reaction section, which $CO_2$ derives from the formation of by-products. Also the off gases coming from the work-up section can be analysed, e.g. either by analysing a combined gas stream coming from the reaction section and the work-up section (la) or via analysing the gas streams separately. Also the phosgene stream can be analysed to see whether and how much $CO_2$ can be found in here so that the background $CO_2$ can be set. The process represented in FIG. 2 allows that the process control can adjust faster in the sequence the process conditions and prevents sooner in the process that further by-products are formed.

Figure 3:
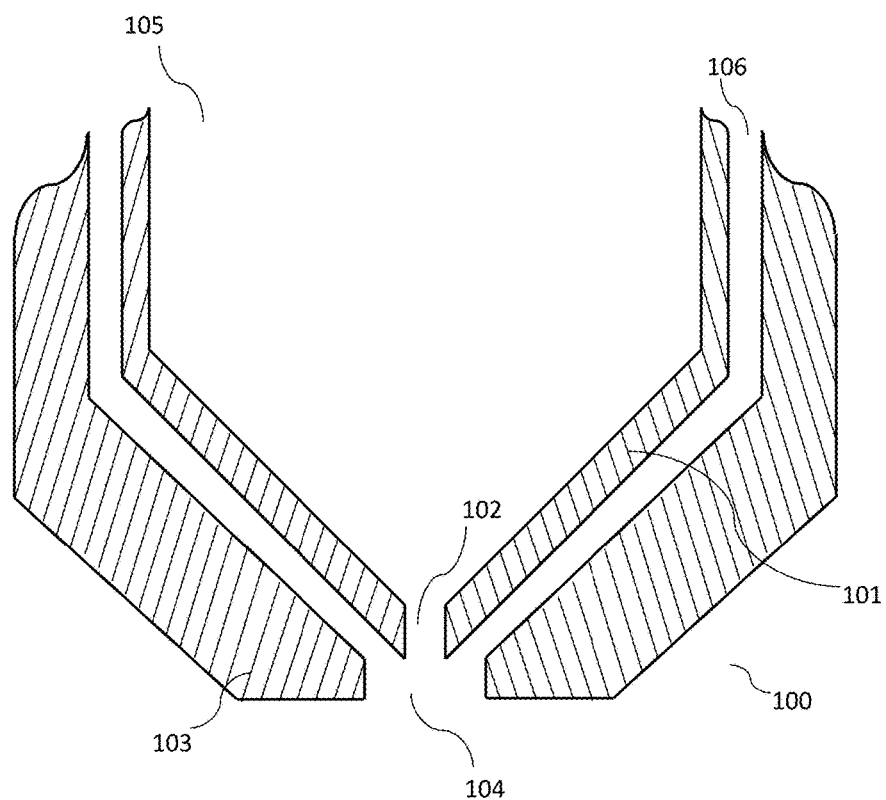
FIG. 3 represents a cross-sectional view of a possible inlet according to the invention.

Referring now to FIG. 3, there is shown an example of an inlet comprising a mixing nozzle for providing the primary aromatic amine stream and the phosgene stream in the reactor. The mixing nozzle is an impinging coaxial assembly 100 comprising an inner conduit 101 having an inner conduit end opening 102 disposed coaxially inside an outer conduit 103 having an outer conduit end opening 104. Flow chamber 105 is defined as the rectangular space inside inner conduit 101 and inner conduit end opening 102. The inner end conduit opening is the place where the phosgene stream or the primary aromatic amine stream is discharged. Flow chamber 106 begins as the rectangular space between outer conduit 101 and inner in conduit end 102. Flow chamber 106 continues as the rectangular space between outer conduit end 104 and inner conduit 101. Flow chamber 106 continues further as the rectangular space between outer conduit end opening 104 and inner conduit end opening 102. The outer end conduit opening 104 is the place where the phosgene stream or the primary aromatic amine stream is discharged, which stream is different than the stream discharged at the inner end conduit opening 102.

EXAMPLE 1

In an industrial plant for making MDI, an MDA stream and a stream of phosgene which is dissolved in MCB are fed via a mixing nozzle in a phosgenation reactor. The gases formed in the reactor are taken off and the reactants are fed to the work-up section. Gases that are formed in the work-up section are combined with the gases coming from the reactor and analysed via infrared spectroscopy to see the amount of $CO_2$. The background $CO_2$ was around 0.10 vol %. The amount of $CO_2$ was considered too high (higher than 0.6 vol %) and the nozzle opening was decreased. This has as a consequence that the back-pressure [p], which is the pressure of the primary amine stream entering the nozzle, increases. This back-pressure can be measured and reflects the size of the nozzle opening.

Figure 4:
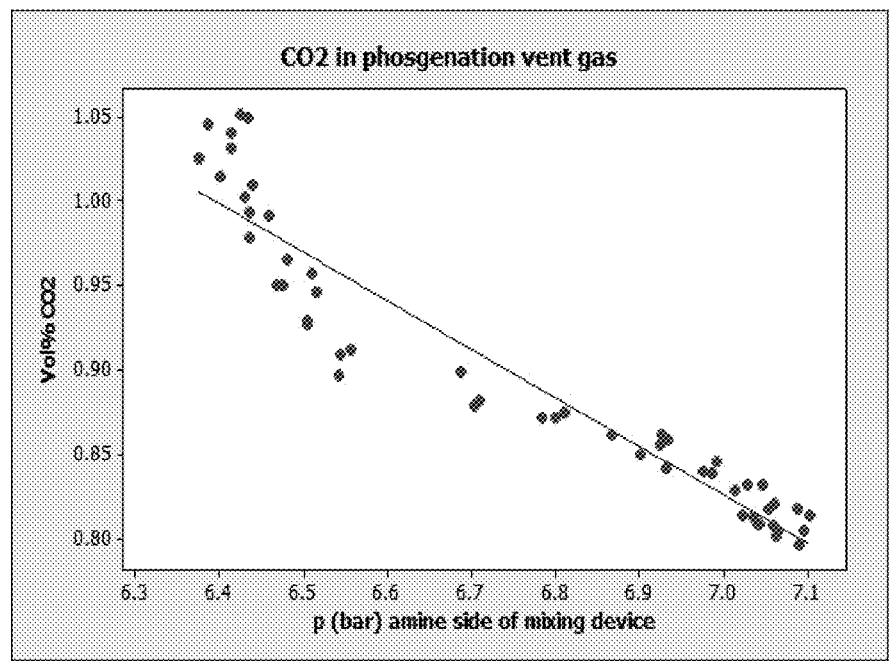
FIG. 4 is a curve showing on the Y axis the amount of $CO_2$ that has been found in the gasses coming from the work-up section and the reaction section and the X axis shows the amount of the back pressure of the primary aromatic amine stream, which is a measure of the inlet opening.

FIG. 4 shows that when the back pressure is higher, and thus the nozzle opening is decreased, less $CO_2$ is measured and thus less by-products have been formed.

The invention claimed is:

1. A method for preparing an aromatic polyisocyanate in an isocyanate plant comprising a reaction section for a phosgenation reaction, the method comprising the steps of:
    a) providing a primary aromatic amine stream and a phosgene stream via an inlet in the reaction section;
    b) reacting the primary aromatic amines with the phosgene compounds in the reaction section to obtain an isocyanate comprising reaction product;
    c1) measuring $CO_2$ concentration in the gases coming from the reaction section;
    d1) analyzing the $CO_2$ concentration coming from the reaction section by comparing with a background $CO_2$ concentration, wherein the background $CO_2$ concentration comprises the $CO_2$ concentration in the phosgene stream;
    e) adjusting conditions in the phosgenation reaction in case the $CO_2$ concentration in the gases coming from the reaction section is higher than a background $CO_2$ concentration and/or deviates with more than 2 vol %, in view of the total volume of the gases coming from the reaction section.

2. A method for preparing an aromatic polyisocyanate in an isocyanate plant comprising a reaction section for a phosgenation reaction and a work-up section which is downstream of the reaction section and treats an isocyanate comprising stream, the method comprising the steps of:
    a) providing a primary aromatic amine stream and phosgene stream via an inlet in the reaction section;
    b) reacting the primary aromatic amine compounds with the phosgene compounds in the reaction section to obtain an isocyanate comprising reaction product;
    c2) measuring $CO_2$ concentration in the gases coming from the reaction section and the work-up section;
    d2) analyzing the $CO_2$ concentration coming from the reaction section and the work-up section by comparing with a background $CO_2$ concentration range;
    e) adjusting conditions in the phosgenation reaction in case the $CO_2$ concentration in the gases coming from the reaction section and the work-up section is higher than a background $CO_2$ concentration and/or deviates with more than 2 vol %, preferably in view of the total volume of the gases coming from the reaction section.

3. The method according to claim 1, wherein the inlet comprises a mixing nozzle having at least two conduits one providing the primary aromatic amine stream and one providing the phosgene stream and of which the conduits have a conduit end opening where the primary aromatic amine stream and phosgene stream are discharged in the reaction section.

4. The method according to claim 3, wherein the adjustment of the conditions of the phosgenation reaction is the adjustment of the size of at least one conduit end opening in the nozzle.

5. The method according to claim 4, wherein the adjustment of the size is decreasing the size of at least one conduit end opening.

6. The method according to claim 3, wherein the adjustment of the conditions of the phosgenation reaction is the adjustment of the angle of at least one of the conduits.

7. The method according to claim 3, wherein the adjustment of the conditions of the phosgenation reaction is the adjustment of the distance between at least two of the conduits.

8. The method according to claim 1, wherein the inlet comprises a mixing device which is a rotor-stator mixer having a rotor and the adjustment of the conditions of the phosgenation reaction is the adjustment of the speed of the rotor.

9. The method according to claim 1, wherein the adjustment of the conditions of the phosgenation reaction is adjusting the flow ratio of the primary aromatic amine compounds stream and the phosgene stream at the inlet of the reaction section, by decreasing or increasing the flow ratio.

10. The method according to claim 1, wherein the adjustment of the conditions of the phosgenation reaction is adjusting the pressure in the reaction section.

11. The method according to claim 1, wherein the adjustment of the conditions of the phosgenation reaction is adjusting the temperature in the reaction section.

12. The method according to claim 1, wherein the adjustment of the conditions of the phosgenation reaction is adjusting the residence time of the reaction mixture of the primary aromatic amine compounds with the phosgene compounds in the reaction section.

13. The method according to claim 1, wherein the adjustment of the conditions of the phosgenation reaction is adjusting the concentration of the primary aromatic amine in the primary aromatic amine stream and/or the phosgene compounds in the phosgene stream.

14. The method according to claim 1, wherein the $CO_2$ concentration is measured via infrared, gas chromatography, titration, near infrared, and/or UV.

15. The method according to claim 1, wherein the background $CO_2$ concentration further comprises the $CO_2$ concentration in the primary aromatic amine stream.

* * * * *